United States Patent
Potnis et al.

(10) Patent No.: US 9,562,254 B2
(45) Date of Patent: Feb. 7, 2017

(54) ANTI-BIOFILM SCREENING ASSAYS

(71) Applicant: Colgate-Palmolive Company, New York, NY (US)

(72) Inventors: Shashank Potnis, Chennai (IN); Navin Lewis, Chennai (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/770,866

(22) PCT Filed: Mar. 19, 2013

(86) PCT No.: PCT/IN2013/000183
§ 371 (c)(1),
(2) Date: Aug. 27, 2015

(87) PCT Pub. No.: WO2014/147629
PCT Pub. Date: Sep. 25, 2014

(65) Prior Publication Data
US 2016/0010137 A1    Jan. 14, 2016

(51) Int. Cl.
*C12Q 1/18* (2006.01)
*G01N 33/569* (2006.01)

(52) U.S. Cl.
CPC ........... *C12Q 1/18* (2013.01); *G01N 33/56955* (2013.01)

(58) Field of Classification Search
CPC ..................................................... C12Q 1/18
See application file for complete search history.

(56) References Cited

U.S. PATENT DOCUMENTS

2013/0177916 A1    7/2013  Chen et al.

FOREIGN PATENT DOCUMENTS

WO    WO 2012/024897    3/2012

OTHER PUBLICATIONS

Saxton et al. Sacnd J Dent Res., 1988, 96:212-217.*
Paryavi-Gholami et al. American Academy of Pediatric Dentistry, 1999, 21(6):320-324.*
Guggenheim et al. J Dent Res., 2001, 80(1):363-370.*
Herles et al., 1994, "Chemostat flow cell system: an in vitro model for the evaluation of antiplaque agents," J. Dental Research 73(11):1748-1755.
Horowitz et al., 1973, "Hydrogen sulfide production in the periodontal environment" J. Periodontology 44(7):390-395.
International Search Report and Written Opinion in International Application No. PCT/IN2013/000183, mailed Dec. 9, 2013.
Kinniment et al., 1996, "The effect of chlorhexidine on defined, mixed culture oral biofilms grown in a novel model system," J. Applied Bacteriology 81(2):120-125.
Lemos, et al., 2010, "Protocols to study the physiology of oral biofilms," Methods Mol Biology 666:87-102.
Saxton et al., 1987, "The effects of a dentifrice containing a zinc salt and a non-cationic antimicrobial agent on plaque and gingivitis," J Clin Periodontology 14(3):144-148.

* cited by examiner

*Primary Examiner* — Bin Shen

(57) ABSTRACT

Procedures are provided to evaluate the effectiveness of slow-acting antibacterial agents such as metal salts on reduction of bacterial oral biofilm. In the modified process, the exposure time of the agent is increased from the usual 3 minutes to 7-15 minutes, e.g., about 10 minutes, and the duration increased to 5-12 days, e.g., about 8 days instead of the conventional 3 days.

7 Claims, No Drawings

ANTI-BIOFILM SCREENING ASSAYS

CROSS-REFERENCE TO RELATED APPLICATIONS

This application is a national stage application under 35 U.S.C. §371 of PCT/IN2013/000183, filed Mar. 19, 2013, the contents of which are incorporated herein by reference in their entirety.

BACKGROUND

Conventional methods of screening compounds for potential efficacy of oral care agents against bacteria typically assess the efficacy of test compounds and compositions in a suspension culture of defined species of bacteria, measuring bacterial proliferation as a function of optical density (OD) in the presence and absence of the test agent, over a short period of time, following a brief exposure to the test agent.

Such assays are very effective to identify potent and fast-acting antibacterial agents, but are poorly suited to identifying optimal antibacterial agents when the agents would have repeated application over longer periods of time (e.g., by daily or twice daily brushing or rinsing).

Moreover, activity against defined microorganisms in suspension culture may not adequately measure activity against the natural microflora, comprising a diversity of species in a biofilm. Bacteria in a biofilm are developmentally and phenotypically different from genetically identical bacteria in a free-floating suspension, and may react differently to antibacterial agents.

Therefore, there is a need for improved assays for identifying and evaluating antibacterial agents effective against oral biofilms.

SUMMARY

Procedures have been developed to evaluate the effectiveness of slow-acting antibacterial agents such as metal salts on reduction of bacterial oral biofilm. In the modified process, the exposure time of the agent is increased from the usual 3 minutes to 7-15 minutes, e.g., about 10 minutes, and the duration increased to 5-12 days, e.g., about 8 days instead of conventional 3 days. This process allows testing of comparatively slow acting antibacterial agents.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope Of the invention.

DESCRIPTION OF THE INVENTION

The following description of the preferred embodiment(s) is merely exemplary in nature and is in no way intended to limit the invention, its application, or uses.

The invention provides, in one embodiment, a method (Method 1) of measuring the efficacy of a test composition (for example a toothpaste or mouthwash) against oral bacterial biofilm growth, comprising
  a) Coating a dental sample, selected from a tooth section and a hydroxyapatite disc, with saliva and placing the sample in a flow of a buffered medium, wherein temperature, flow and pH adjusted to approximate conditions in the mouth and wherein the buffered medium comprises nutrients similar to those in the mouth;
  b) Exposing the dental sample to a test composition, then reinstating the flow of buffered medium, wherein the period of exposure to a test compound is from 7-15 minutes, e.g. 8-12 minutes, e.g., about 10 minutes;
  c) Repeating the preceding step from one to four times per day for 5-12 days, e.g., for 6-10 days, e.g., for about 8 days;
  d) Vortexing the dental sample in anaerobic media to obtain a suspension and measuring the optical density thereof, wherein a lower optical density indicates that the test composition is more effective against oral biofilm growth.

For example, the invention provides
  1.1. Method 1 wherein the period of exposure the dental sample to a test composition in step b) is for a period of about 10 minutes.
  1.2. Method 1 or 1.1 wherein the step of repeating step b) is carried out from one to four times per day for about 8 days:
  1.3. Any preceding method wherein the buffered medium comprises nutrients as required to support bacterial growth, e.g., comprising phosphate buffer, sugar, amino acids, and essential vitamins and minerals.
  1.4. Any preceding method further comprising the step of culturing the suspension on a solid media and counting the number of colony forming units after a period of 2-5 days, wherein a lower number of colony forming units indicates that the test composition is more effective against oral biofilm growth.
  1.5. Method 1.4 wherein the culture on solid media is carried out in the presence of a metal salt, e.g., an iron or lead salt, which reacts with a volatile sulfur compound formed in step a-c, e.g., hydrogen sulfide, to form a black precipitate, e.g., a metal sulfide.
  1.6. Method 1.5 wherein the solid media is an agar plate and the metal salt is lead acetate.
  1.7. Method 1.4 or 1.5 wherein any black colony forming units are counted independently from the other colony forming units and wherein a lower number of black colony forming units indicates that the test composition is more effective against oral biofilm growth comprising bacteria that produce volatile sulfur compounds.
  1.8. Any preceding method wherein the test composition is an oral care product.
  1.9. Any preceding method wherein the test composition comprises at least 0.1% of a metal ion having a valence of +2 or +3, e.g. $Zn^{2+}$ or $Sn(II)^{2+}$.
  1.10. Method 1.9 comprising measuring the uptake of the metal ion from the test composition by the dental sample, wherein greater uptake of the metal ion by the dental sample corresponds to the greater efficacy of the oral care product against oral biofilm formation.

Buffered medium as used in step a) above may be any suitable medium as known in the art for allowing biofilm growth. See, for example, the various media described in Lemos, et al., Methods Mol Biol. 2010; 666: 87-102, the contents of which are incorporated herein by reference. A typical medium thus comprises phosphate buffer, sugar, amino acids, and essential vitamins and minerals, and is adjusted to approximately pH and osmolality approximating natural saliva.

For example, one exemplary medium is made up of 58 mM $K_2HPO_4$, 15 mM $KH_2PO_4$, 10 mM $(NH_4)2SO_4$, 35 mM NaCl, 0.8% (wt/vol) glucose, 0.2% (wt/vol) Casamino Acids (CAA), and 100 mM $MnCl_2.4H_2O$ (pH 7.4) and is supplemented with filter-sterilized vitamins (0.04 mM nicotinic acid, 0.1 mM pyridoxine HCl, 0.01 mM pantothenic acid, 1 µM riboflavin, 0.3 µM thiamin HCl, and 0.05 µM d-biotin), amino acids (4 mM 1-glutamic acid, 1 mM L-arginine HCl, 1.3 mM 1-cysteine HCl, and 0.1 mM 1-tryptophan), and 2 mM $MgSO_2.7H_2O$.

The dental samples as used herein are preferably saliva-coated hydroxyapatite discs. The saliva inoculates the discs with natural oral bioflora. Hydroxyapatite discs are commercially available, e.g., from Clarkson Chromatography Products, Inc. Hydroxyapatite, also called hydroxyapatite, is a naturally occurring mineral form of calcium apatite with the formula $Ca_5(PO_4)_3(OH)$. The formula is usually written $Ca_{10}(PO_4)_6(OH)_2$ to denote that the crystal unit cell comprises two entities. Dental enamel and dentin arc comprised primarily of carbonated calcium-deficient hydroxyapatite.

Use of metal salts to detect the presence Of bacteria producing volatile sulfur compounds is based on the fact that volatile sulfides such as hydrogen sulfide react with metal ions, for example $Fe(II)^{++}$ or $Pb(II)^{++}$, to form metal sulfides, which may be considered the salts of hydrogen sulfide. Metal sulfides generally have a dark color. Lead(II) acetate paper or media may be used to detect hydrogen sulfide, for example, because it turns grey or black in the presence of the gas as lead(II) sulfide is produced. Various media containing iron compounds also allow detection of hydrogen sulfide production, for example Sulfide-Indole-Motility (SIM) medium or triple sugar iron agar (TSIA), both of which contain $Fe(II)^{++}$, which reacts with hydrogen sulfide to produce FeS as a black precipitate.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Embodiments of the present invention are further described in the following examples. The examples are merely illustrative and do not in any way limit the scope of the invention as described and claimed.

Example 1

Conventional Protocol Design

A method of dynamic biofilm system based on conventional protocols is used to study the effect of actives on oral biofilm developed from salivary microflora. Saliva coated hydroxyapatite (HAP) discs are placed in the flow cell and connected to a one flow medium passage. The medium flows from the reservoir through the flow cells and is removed as the waste. Untreated sample/placebo is used as a control to test the efficacy of the dentifrices. Treatment solutions of 1:10 diluted dentifrices (30 ml) are then drawn into the flow cells to contact the disks for 1 minute. The flow of media is reinstated to rinse the treated discs and further allow the growth of biofilm during the study period of three days. The treatment is repeated over a time interval of 24 hours with the flow adjusted to stimulate conditions in the human mouth.

The HAP discs are collected at the end of the study and introduced into anaerobic media, and vortexed to make the plaque on the disc thoroughly suspend in the solution. 300 µl of the suspension is pipeted into the wells of a 96-well microplate, and the optical density (OD) at 610 nm is read using a microplate reader. Means and standard deviation of the different treatments are calculated. The lower the OD, the lower the bacteria level, and the better the efficacy of the treatment.

The suspension from the flowcell is collected and diluted serially with anaerobic transfer media. Serial dilutions are plated on lead acetate plates and incubated anaerobically at 37° C. for 2-3 days. The real colony forming units on the HAP disc are counted and the final result is reported as Log cfu/disc. The lower the value, the better the efficacy of the treatment.

The lead acetate reacts with sulfur to form a black deposit, so the black colonies on the plates can be counted independently as an evaluation for a product's efficacy against bacteria producing volatile sulfur compounds. This is of interest because bacteria which produce volatile Sulfur compounds are thought to be major contributors to halitosis.

Prototype formulations are prepared as set forth in the table below.

TABLE 1

Comparison of different zinc prototype formulations

| Ingredients | Control (CAS) % | Option 1 1% ZnO in chalk % | Option 2 1% ZnO + 0.5% Zn Citrate in chalk % | Option 3 2% Zn Citrate in silica % | Option 4 0.5% ZnO + 2% Zn Citrate in silica % | Option 5 1% ZnO in silica % | Option 6 1% ZnO + 0.5% Zn Citrate in silica % |
|---|---|---|---|---|---|---|---|
| Sorbitol(70%) | 21 | 21 | 21 | 22 | 22 | 55 | 55 |
| PEG 600 | — | — | — | 2 | 2 | 2 | 2 |
| Trimethyl glycine | — | — | — | — | — | 1.25 | 1.25 |
| Xanthan | 0.2 | 0.3 | 0.3 | 0.3 | 0.3 | 0.3 | 0.3 |
| Purified Water | 28.9 | 28.1 | 27.59 | 44.59 | 45.09 | 15.54 | 15.04 |
| Carboxymethyl cellulose TMS | 0.72 | 0.75 | 0.75 | — | — | — | — |
| Carboxymethyl cellulose 2000S | — | — | — | 1.2 | 1.2 | 0.8 | 0.8 |
| Sodium Saccharin | 0.27 | 0.35 | 0.35 | 0.3 | 0.3 | 0.3 | 0.3 |
| Sodium monofluorophosphate | 0.76 | 0.76 | 0.76 | 0.76 | 0.76 | 0.76 | 0.76 |
| Sodium bicarbonate | 0.5 | 1.0 | 1.0 | — | — | — | — |
| NaOH 50% | 0.1 | — | — | — | — | — | — |
| MFIL-P | 2.5 | 0.5 | 0.5 | 5 | 4 | 4 | 4 |
| Silica abrasive (ZEO 114) | — | — | — | 10 | 10 | 10 | 10 |

TABLE 1-continued

Comparison of different zinc prototype formulations

| Ingredients | Control (CAS) % | Option 1 1% ZnO in chalk % | Option 2 1% ZnO + 0.5% Zn Citrate in chalk % | Option 3 2% Zn Citrate in silica % | Option 4 0.5% ZnO + 2% Zn Citrate in silica % | Option 5 1% ZnO in silica % | Option 6 1% ZnO + 0.5% Zn Citrate in silica % |
|---|---|---|---|---|---|---|---|
| Precipitated calcium carbonate (PCC) | 18 | — | — | — | — | — | — |
| Refined natural calcium carbonate (NCC) | 22.5 | — | — | — | — | — | — |
| NCC-India | — | 35 | 35 | — | — | — | — |
| Sodium lauryl sulfate | 2. | 2.0 | 2.0 | 2 | 2. | 2 | 2 |
| Benzyl alcohol | 0.3 | 0.3 | 0.3 | 0.3 | 0.3 | 0.3 | 0.3 |
| Flavor | 1 | 1.2 | 1.2 | 1.3 | 1.3 | 1.3 | 1.3 |
| Tetrasodium pyrophosphate (TSPP) | 0.5 | 1 | 1 | 1 | 1 | 0.5 | 0.5 |
| Tetrapotassium pyrophosphate (TKPP) | — | 1 | 1 | 2 | 2 | — | — |
| Zinc oxide | — | 1 | 1 | — | 0.5 | 1 | 1 |
| Zinc citrate | — | — | 0.5 | 2 | 2 | — | 0.5 |
| Titanium dioxide | 0.75 | 0.75 | 0.75 | — | — | — | — |
| Pearlescent white pigment (Timiron ®) | — | — | — | — | 0.25 | 0.25 | 0.25 |
| Small particle silica (AC43) | — | 5 | 5 | 5 | 5 | 5 | 5 |
| Total | 100 | 100 | 100 | 100 | 100 | 100 | 100 |

The results of the study with the above-described method (3 days) are outlined in Tables 2-4 below. The formulations tested include the prototype formulations, and also commercial toothpaste products Colgate Total® and Crest Pro-Health, which contain triclosan and stannous fluoride respectively as antibacterial agents.

TABLE 2

OD at 610 nm of the harvested HAP disc with three different inoculum sources (3 day study) - data grouped with Tukey method at 95% confidence level

| Sample Description | Subject 1 Avg. | Subject 2 Avg. | Subject 3 Avg. | Mean |
|---|---|---|---|---|
| CAS control | 0.43 | 0.59 | 0.33 | 0.45 |
| Crest ® ProHealth HW (2% Zinc citrate) | 0.31 | 0.46 | 0.24 | 0.34 |
| 1% ZnO in chalk | 0.24 | 0.47 | 0.19 | 0.30 |
| 360 WMH (2% Zn citrate) | 0.25 | 0.33 | 0.23 | 0.27 |
| 1% ZnO + 0.5% Zn citrate in chalk | 0.08 | 0.37 | 0.36 | 0.27 |
| 1% ZnO in silica | 0.15 | 0.47 | 0.12 | 0.25 |
| 1% ZnO + 0.5% Zinc citrate in silica | 0.23 | 0.28 | 0.22 | 0.24 |
| Total ® whitening (triclosan) | 0.19 | 0.19 | 0.16 | 0.18 |

TABLE 3

Values of plate count on Neomycin Vancomycin agar (3 day study) - data grouped with Tukey method at 95% confidence level

| Sample Description | Subject 1 log CFU/disc | Subject 2 log CFU/disc | Subject 3 log CFU/disc | Mean |
|---|---|---|---|---|
| CAS control | 7.01 | 7.06 | 6.93 | 7.00 |
| 1% ZnO in chalk | 6.66 | 6.80 | 6.87 | 6.78 |
| 1% ZnO + 6.5% Zn citrate in chalk | 6.63 | 6.78 | 6.71 | 6.71 |
| 360 WMH (2% Zn citrate) | 6.57 | 6.66 | 6.74 | 6.66 |
| Crest ® ProHealth HW (2% Zinc citrate) | 6.59 | 6.64 | 6.54 | 6.59 |
| 1% ZnO in silica | 6.53 | 6.40 | 6.54 | 6.49 |
| 1% ZnO + 0.5% Zinc citrate in silica | 6.09 | 6.36 | 6.50 | 6.32 |
| Total ® whitening (triclosan) | 5.26 | 4.92 | 5.94 | 5.38 |

CFU—colony forming units

TABLE 4

Values of plate count on Lead Acetate agar (3 day study) - data grouped with Tukey method at 95% confidence level

| Sample Description | Subject 1 log CFU/disc | Subject 2 log CFU/disc | Subject 3 log CFU/disc | Mean |
|---|---|---|---|---|
| CAS control | 6.75 | 6.89 | 6.82 | 6.82 |
| 1% ZnO in chalk | 6.53 | 6.69 | 6.77 | 6.66 |
| 1% ZnO + 0.5% Zn citrate in chalk | 6.39 | 6.63 | 6.48 | 6.50 |
| Crest ® ProHealth HW (2% Zinc citrate) | 6.36 | 6.52 | 6.16 | 6.38 |
| 1% ZnO in silica | 6.31 | 6.26 | 6.41 | 6.33 |
| 360 WMH (2% Zn citrate) | 5.91 | 6.02 | 6.11 | 6.01 |
| 1% ZnO + 0.5% Zinc citrate in silica | 5.72 | 5.84 | 5.94 | 5.83 |
| Total ® whitening (triclosan) | 5.04 | 5.08 | 5.53 | 5.22 |

CFU—colony forming units

Example 2

Modified Dynamic Biofilm Protocol Design

The experiment is then modified to be more representative of the actual in vivo situation. Saliva coated HAP disks are placed in the flow cell and connected to a one flow medium passage. The medium flows from the reservoir through the flow cells and is removed to waste. Untreated sample/placebo is used as a control to test the efficacy of the dentrifices. Treatment solutions of 1:10 diluted dentifrices (30 ml) are then drawn into the flow cells to contact the disks for 10 minutes. The flow of media is reinstated to rinse the treatment and further allow the growth of biofilm during the study period. The treatment is repeated over a time interval of 24 hours with the flow adjusted to stimulate conditions in the human mouth.

The treatment regime is increased to 8 days. The HAP disks are collected at the end of the study and introduced into anaerobic media, and vortexed to suspend the plaque on the disc thoroughly in the solution. 300 µl of the suspension is pipetted into the wells of a 96-well microplate, and optical density (OD) is read at 610 nm in the microplate reader. An Excel spreadsheet is used to calculate means and standard deviation of the different treatments. The lower the OD, the better the efficacy of the treatment.

The suspension from the flowcell is collected and diluted serially with anaerobic transfer media. Serial dilutions are plated on lead acetate plates and incubated anaerobically at 37° C. for 2-3 days. The real colony forming units on the HAP disc are counted and the final result reported as Log CFU/disc. The lower the value, the better the efficacy of the treatment.

The black colonies on the plates are counted independently as an evaluation for the product's anti-VSC efficacy.

The following changes are made to the more conventional method of example 1 with respect to treatment—biofilm interaction, while keeping the working principle of the method constant. In the modified method the treatment regime is increased to 8 days in place of 3 days. The contact time is also increased to 10 minutes from 1 minute. The rest of the procedure is repeated as is with harvesting after completion of 8 days. The differentiation between in the individual values of the results is found to be significant.

The results are summarized in Tables 5-7 below:

TABLE 5

OD at 610 nm of the harvested HAP disc with three different inoculum sources (8 day study) - data grouped with Tukey method at 95% confidence level

| Sample Description | Subject 1 Avg. | Subject 2 Avg. | Subject 3 Avg. | Mean |
|---|---|---|---|---|
| CAS control | 1.50 | 1.36 | 1.44 | 1.43 |
| Crest ® ProHealth HW (2% Zinc citrate) | 1.12 | 1.18 | 1.20 | 1.17 |
| 1% ZnO in chalk | 1.10 | 1.04 | 0.94 | 1.03 |
| 1% ZnO + 0.5% Zn citrate in chalk | 0.82 | 0.76 | 0.92 | 0.84 |
| 360 WMH (2% Zn citrate) | 0.64 | 0.58 | 6.66 | 6.63 |
| 1% ZnO in silica | 0.51 | 0.62 | 0.68 | 0.60 |
| 1% ZnO + 0.5% Zinc citrate in silica | 0.35 | 0.48 | 0.42 | 0.42 |
| Total ® whitening (triclosan) | 0.25 | 0.31 | 0.34 | 0.30 |

TABLE 6

Values of plate count on Neomycin Vancomycin agar (8 day study) - data grouped with Tukey method at 95% confidence level

| Sample Description | Subject 1 log CFU/disc | Subject 2 log CFU/disc | Subject 3 log CFU/disc | Mean |
|---|---|---|---|---|
| CAS control | 7.32 | 7.46 | 7.55 | 7.44 |
| Crest ® ProHealth HW (2% Zinc citrate) | 7.00 | 6.64 | 6.54 | 6.73 |
| 1% ZnO in chalk | 6.28 | 6.24 | 6.49 | 6.34 |
| 1% ZnO + 0.5% Zn citrate in chalk | 5.95 | 6.12 | 6.20 | 6.09 |
| 360 WMH (2% Zn citrate) | 5.85 | 6.02 | 6.35 | 6.08 |
| 1% ZnO in silica | 5.72 | 5.98 | 6.04 | 5.91 |
| 1% ZnO + 0.5% Zinc citrate in silica | 5.67 | 5.75 | 5.59 | 5.67 |
| Total ® whitening (triclosan) | 4.95 | 4.86 | 5.02 | 4.94 |

CFU—colony forming units

TABLE 7

Values of plate count on Lead Acetate agar (8 day study) - data grouped with Tukey method at 95% confidence level

| Sample Description | Subject 1 log CFU/disc | Subject 2 log CFU/disc | Subject 3 log CFU/disc | Mean |
|---|---|---|---|---|
| CAS control | 6.13 | 6.24 | 6.49 | 6.28 |
| 1% ZnO in chalk | 5.82 | 5.74 | 5.95 | 5.84 |
| Crest ® ProHealth HW (2% Zinc citrate) | 5.72 | 5.56 | 5.63 | 5.63 |
| 1% ZnO + 0.5% Zn citrate in chalk | 5.58 | 5.46 | 5.60 | 5.55 |
| 360 WMH (2% Zn citrate) | 5.65 | 5.46 | 5.37 | 5.49 |
| 1% ZnO in silica | 5.11 | 5.35 | 5.16 | 5.21 |
| 1% ZnO + 0.5% Zinc citrate in silica | 4.88 | 4.95 | 5.04 | 4.96 |
| Total ® whitening (triclosan) | 4.76 | 4.92 | 4.06 | 4.56 |

CFU—colony forming units

The modified method of this example is not only closer to the natural situation, but it does a better job of distinguishing the relative antibacterial activities of the different formulations. While the commercial Total® formulation, which contains a potent antibacterial agent (triclosan) was always the most effective, the different formulations with different metal salts proved to have good activities over time, and as seen from the Tukey analysis, these differences allow separation and ranking of the different formulations, which was not possible using conventional testing, which had these formulations as statistically indistinguishable.

Example 3

Comparative Evaluation Between Data for 3 Days (Conventional) and 8 Days (Modified) Study The mean data for each prototype was compared using each of the two methods. The modified method is able to effectively differentiate statistically between the positive control (Total whitening (triclosan)) and the negative control (CAS control), and moreover is able to distinguish between different prototypes using different Zn compound combinations. This allows better selection and optimization of lead formulation based on efficacy.

TABLE 8

Mean values of OD at 610 nm for conventional and modified method

| Sample Description | 3 day study | 8 day study |
| --- | --- | --- |
| CAS control | 0.45 | 1.43 |
| Crest ® ProHeatth HW (2% Zinc citrate) | 0.34 | 1.17 |
| 1% ZnO in chalk | 0.30 | 1.03 |
| 1% ZnO + 0.5% Zn citrate in chalk | 0.27 | 0.84 |
| 360 WMH (2% Zn citrate) | 0.27 | 0.63 |
| 1% ZnO in silica | 0.25 | 0.60 |
| 1% ZnO + 0.5% Zinc citrate in silica | 0.24 | 0.42 |
| Total ® whitening (triclosan) | 0.18 | 0.30 |

TABLE 9

Mean values of plate count on NV agar with conventional and modified method

| Sample Description | 3 day study | 8 day study |
| --- | --- | --- |
| CAS control | 7.00 | 7.44 |
| Crest ® ProHealth HW (2% Zinc citrate) | 6.59 | 6.73 |
| 1% ZnO in chalk | 6.78 | 6.34 |
| 1% ZnO + 0.5% Zn citrate in chalk | 6.71 | 6.09 |
| 360 WMH (2% Zn citrate) | 6.66 | 6.08 |
| 1% ZnO in silica | 6.49 | 5.91 |
| 1% ZnO + 0.5% Zinc citrate in silica | 6.32 | 5.67 |
| Total ® whitening (triclosan) | 5.38 | 4.94 |

CFU—colony forming units

TABLE 10

Mean values of plate count on Lead Acetate agar with conventional and modified method

| Sample Description | 3 day study | 8 day study |
| --- | --- | --- |
| CAS control | 6.82 | 6.28 |
| 1% ZnO in chalk | 6.66 | 5.84 |
| Crest ® ProHealth HW (2% Zinc citrate) | 6.38 | 5.63 |
| 1% ZnO + 0.5% Zn citrate in chalk | 6.50 | 5.55 |
| 360 WMH (2% Zn citrate) | 6.01 | 5.49 |
| 1% ZnO in silica | 6.33 | 5.21 |
| 1% ZnO + 0.5% Zinc citrate in silica | 5.83 | 4.96 |
| Total ® whitening (triclosan) | 5.22 | 4.56 |

CFU—colony forming units

Example 4

Correlation Between Zn Uptake and Biofilm Reduction Data for Conventional and Modified Method The average amount of Zn uptake on HAP is a direct measure of the ability of the compound to reduce biofilm in vivo. Over a short interval, zinc citrate has a higher uptake, but with a longer time interval, the uptake of zinc oxide increases. Thus, the available zinc is enhanced with multiple treatments of zinc oxide, resulting in increased biofilm reduction.

TABLE 11

Average values of Zn uptake on HAP using AAS with both methods

| Sample Description | Uptake µg/HAP | |
| --- | --- | --- |
| | 3 day study | 8 day study |
| Crest ® ProHealth HW (2% Zinc citrate) | 52 | 17 |
| 360 WMH (2% Zn citrate) | 47 | 56 |
| 1% ZnO in chalk | 77 | 99 |
| 1% ZnO + 0.5% Zn citrate in chalk | 77 | 116 |
| 1% ZnO in silica | 85 | 186 |
| 1% ZnO + 0.5% Zinc citrate in silica | 73 | 190 |

As can be seen from the data in Table 11, the two samples with the best degree of zinc uptake also correlated with the two best samples in the 8 day biofilm protocols (i.e. 1% ZnO in silica and 1% ZnO+0.5% Zinc citrate in silica)

As those skilled in the art. will appreciate, numerous changes and modifications may be made to the embodiments described herein without departing from the spirit of the invention. It is intended that all such variations fall within the scope of the appended claims.

We claim:

1. A method of measuring the efficacy of a test composition against oral bacterial biofilm formation, comprising
   a) Coating a sample with saliva and placing the sample in a flow of a buffered medium, with temperature, flow and pH adjusted to approximate conditions in the mouth; wherein the sample is selected from a tooth section and hydroxyapatite disc;
   b) Exposing the sample to a test composition, then reinstating the flow of buffered medium, wherein the period of exposure to a test compound is from 7-15 minutes;
   c) Repeating the preceding step from one to four times per day for 5-12 days;
   d) Vortexing the sample in anaerobic media to obtain a suspension and measuring the optical density thereof, wherein the optical density is a measure of the degree of bacterial growth;
   e) Culturing the suspension on a solid media and counting the number of colony forming units after a period of 2-5 days, wherein the number of colony forming units is a measure of the degree of bacterial growth, and wherein the culturing is carried out in the presence of a metal salt which reacts with volatile sulfur compounds formed in steps a-c to form a black precipitate; and
   wherein said test composition further comprises zinc oxide and zinc citrate.

2. The method of claim 1 wherein the period of exposure the sample to a test composition in step b) is for a period of about 10 minutes.

3. The method of claim 1 wherein the step of repeating step b) is carried out from one to four times per day for about 8 days.

4. The method of claim 1 wherein the buffered medium comprises nutrients as required to support bacterial growth.

5. The method of claim 1 wherein the solid media is an agar plate and the metal salt is lead acetate.

6. The method of claim 1 wherein any black colony forming units are counted independently from the other colony forming units and wherein the number of black colony forming units corresponds to the degree of growth of bacteria which produce volatile sulfur compounds.

7. The method of claim 1 wherein the test composition is an oral care product.

\* \* \* \* \*